(12) United States Patent
Guthart et al.

(10) Patent No.: US 12,178,667 B2
(45) Date of Patent: Dec. 31, 2024

(54) CLAMP ASSEMBLY FOR FIXING A NAVIGATION TRACKER TO A PORTION OF BONE

(71) Applicant: MAKO Surgical Corp., Weston, FL (US)

(72) Inventors: Matthew Joseph Guthart, Miami, FL (US); Mark Ellsworth Nadzadi, Batavia, OH (US); Andrew Jacob Nelson, New York City, NY (US)

(73) Assignee: MAKO Surgical Corp., Weston, FL (US)

( * ) Notice: Subject to any disclaimer, the term of this patent is extended or adjusted under 35 U.S.C. 154(b) by 498 days.

(21) Appl. No.: 17/673,055

(22) Filed: Feb. 16, 2022

(65) Prior Publication Data

US 2022/0257334 A1      Aug. 18, 2022

Related U.S. Application Data

(60) Provisional application No. 63/149,928, filed on Feb. 16, 2021.

(51) Int. Cl.
  *A61B 90/35*   (2016.01)
  *A61B 17/70*   (2006.01)
  *A61B 90/00*   (2016.01)
  *A61B 90/14*   (2016.01)
(52) U.S. Cl.
  CPC ...... *A61B 90/39* (2016.02); *A61B 2090/3916* (2016.02); *A61B 2090/3991* (2016.02)

(58) Field of Classification Search
  CPC .... A61B 2090/3916; A61B 2090/3991; A61B 17/66; A61B 17/7047; A61B 2017/681; A61B 90/14
  See application file for complete search history.

(56) References Cited

U.S. PATENT DOCUMENTS

| | | | |
|---|---|---|---|
| 3,835,861 A * | 9/1974 | Kees, Jr. | A61B 90/14 403/80 |
| 5,944,723 A | 8/1999 | Colleran et al. | |
| 6,079,896 A | 6/2000 | Dellach | |
| 6,226,548 B1 | 5/2001 | Foley et al. | |
| 6,719,757 B2 | 4/2004 | Neubauer et al. | |
| 7,107,091 B2 | 9/2006 | Jutras et al. | |
| 7,993,353 B2 | 8/2011 | Roeßner et al. | |
| 8,002,772 B2 | 8/2011 | Sarin et al. | |
| 8,192,449 B2 | 6/2012 | Maier et al. | |
| 8,277,454 B2 | 10/2012 | Neubauer et al. | |

(Continued)

*Primary Examiner* — Nicholas W Woodall
(74) *Attorney, Agent, or Firm* — Howard & Howard Attorneys PLLC

(57) ABSTRACT

A clamp assembly fixes a navigation tracker to a bone. The assembly includes first and second clamp jaws. The second clamp jaw is pivotal about a first fixed pivot. A linear driver includes a shaft. A first linkage is pivotal at one end about a second fixed pivot and coupled at an opposing end to the shaft at a first moving pivot. A second linkage is coupled at one end to the shaft at the first moving pivot and coupled at the other end to the second clamp jaw at a second moving pivot. The linear driver linearly translates the shaft to apply force to the first moving pivot in a first direction to pivot the second clamp jaw towards the first clamp jaw and in a second direction opposite to the first direction to pivot the second clamp jaw away from the first clamp jaw.

20 Claims, 6 Drawing Sheets

(56) References Cited

U.S. PATENT DOCUMENTS

| | | |
|---|---|---|
| 8,535,329 B2 | 9/2013 | Sarin et al. |
| 9,008,757 B2 | 4/2015 | Wu |
| 9,101,412 B2 | 8/2015 | Bootwala et al. |
| 9,119,655 B2 | 9/2015 | Bowling et al. |
| 9,179,984 B2 | 11/2015 | Teichman et al. |
| 9,566,121 B2 | 2/2017 | Staunton et al. |
| 9,775,650 B2 | 10/2017 | Buttermann |
| 9,937,058 B2 | 4/2018 | Axelson, Jr. et al. |
| 9,951,904 B2 | 4/2018 | Perez et al. |
| 9,993,273 B2 | 6/2018 | Moctezuma de la Barrera et al. |
| 10,098,672 B2 | 10/2018 | Moskowitz et al. |
| 10,537,395 B2 | 1/2020 | Perez |
| 2002/0049377 A1* | 4/2002 | Moctezuma De La Barrera ........ A61B 90/39 600/407 |
| 2004/0019263 A1* | 1/2004 | Jutras .................... A61B 90/39 600/407 |
| 2004/0068260 A1 | 4/2004 | Cossette et al. |
| 2004/0068263 A1 | 4/2004 | Chouinard et al. |
| 2005/0149028 A1 | 7/2005 | Birkbeck et al. |
| 2005/0149050 A1 | 7/2005 | Stifter et al. |
| 2005/0215888 A1 | 9/2005 | Grimm et al. |
| 2005/0245808 A1 | 11/2005 | Carson |
| 2005/0277832 A1 | 12/2005 | Foley et al. |
| 2006/0004379 A1 | 1/2006 | Sanders et al. |
| 2006/0100638 A1 | 5/2006 | Sarin et al. |
| 2007/0122233 A1 | 5/2007 | Maier et al. |
| 2008/0103512 A1 | 5/2008 | Gately |
| 2008/0221625 A1 | 9/2008 | Hufner et al. |
| 2009/0024127 A1 | 1/2009 | Lechner et al. |
| 2009/0062869 A1* | 3/2009 | Claverie ............ A61B 17/8866 606/151 |
| 2009/0227865 A1 | 9/2009 | Plassky et al. |
| 2013/0113150 A1 | 5/2013 | Velez |
| 2015/0282735 A1 | 10/2015 | Rossner |
| 2016/0015430 A1 | 1/2016 | Buttermann |
| 2016/0281920 A1 | 9/2016 | Perez et al. |
| 2017/0119478 A1 | 5/2017 | Malackowski et al. |
| 2017/0281202 A1 | 10/2017 | Hampp et al. |
| 2018/0092667 A1* | 4/2018 | Heigl ................. A61B 17/7047 |
| 2018/0110572 A1 | 4/2018 | Flatt |
| 2018/0193097 A1 | 7/2018 | Mclachlin et al. |
| 2018/0318035 A1* | 11/2018 | Mclachlin .............. A61B 90/94 |
| 2020/0129264 A1* | 4/2020 | Onativia ................ A61B 90/90 |
| 2021/0038276 A1 | 2/2021 | Schwägli et al. |
| 2021/0338299 A1 | 11/2021 | El-Chafei et al. |
| 2022/0031370 A1 | 2/2022 | Zehavi et al. |
| 2022/0125496 A1 | 4/2022 | López Del Pueyo et al. |
| 2022/0240909 A1 | 8/2022 | Schoen et al. |
| 2023/0073858 A1* | 3/2023 | Boehm, Jr. ........ A61B 17/7014 |

* cited by examiner

CLAMP ASSEMBLY FOR FIXING A NAVIGATION TRACKER TO A PORTION OF BONE

CROSS-REFERENCE TO RELATED APPLICATIONS

The subject application is a U.S. Nonprovisional Patent Application claiming the benefit of and priority to U.S. Provisional Patent Application No. 63/149,928, filed Feb. 16, 2021, the entire contents of which are hereby incorporated by reference in their entirety.

TECHNICAL FIELD

The present disclosure relates generally to a clamp assembly for use with a surgical attachment system for fixing a navigation tracker to a portion of bone.

BACKGROUND

Navigation systems assist users in locating objects. Navigation systems may employ light signals, sound waves, magnetic fields, radio frequency signals, etc. in order to track the position and/or orientation of objects. A localizer cooperates with tracking elements on tracking devices to ultimately determine a position and orientation of the objects. Navigation systems are often used in industrial, aerospace, defense, and medical applications. In the medical field, navigation systems assist surgeons in placing surgical instruments relative to a patient's anatomy. Exemplary surgeries in which navigation systems are used include neurosurgery and orthopedic surgery.

Often the navigation system includes attaching the tracking device to an anatomic object, typically bony anatomy, with a bone screw or other suitable fastener. Once secured to the bony anatomy, and particularly after the tracking device is registered with the localizer, it is important that the tracking device does not move relative to the anatomy. Misalignment due to movement of the tracking device relative to the anatomy can require recalibration or re-registration of the tracking device, or if unnoticed, can result in serious consequences during the surgical procedure, including inadvertent collision with critical anatomic structures, sub-optimally located surgical hardware, and the like.

Clamp mechanisms utilizing scissoring jaws have been utilized that clamp to the bone, after which the tracking device is coupled to the bone. Although useful, the scissoring jaws are limited in the amount of force they can exert on the bone as well as size of bones that can fit between the jaws. Furthermore, prior clamping mechanisms present a relatively large footprint, which may not be conducive for procedures having limited access angle or incision size. Therefore, a need exists in the art for a tracking device that addresses at least the aforementioned problems.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a clamp assembly for use with a surgical attachment system for fixing a navigation tracker to a portion of bone is provided. The clamp assembly comprises a first clamp jaw comprising a first engagement surface and a second clamp jaw comprising a second engagement surface. The second clamp jaw faces the first clamp jaw and is pivotal about a first fixed pivot that is fixed relative to the first clamp jaw. The clamp assembly further comprises a linear driver comprising a linearly translating shaft. The clamp assembly further comprises a first linkage pivotal at one end about a second fixed pivot that is fixed relative to the first clamp jaw and coupled at an opposing end to the shaft at a first moving pivot. The clamp assembly further comprises a second linkage coupled at one end to the shaft at the first moving pivot, and coupled at the other end to the second clamp jaw at a second moving pivot. The linear driver is configured to linearly translate the shaft to apply force to the first moving pivot in a first direction to pivot the second clamp jaw towards the first clamp jaw, and to apply force to the first moving pivot in a second direction opposite to the first direction to pivot the second clamp jaw away from the first clamp jaw.

According to a second aspect, a surgical attachment system for fixing a navigation tracker to a portion of bone is provided. The surgical attachment system comprises an extension arm with a first end and a second end. An arm axis is defined between the first and second ends. The surgical attachment system further comprises an attachment interface at the first end of the extension arm and configured to selectively couple with the navigation tracker, and a clamp assembly disposed at the second end of the extension arm. The clamp assembly comprises a first clamp jaw comprising a first engagement surface and a second clamp jaw comprising a second engagement surface. The second clamp jaw faces the first clamp jaw and is pivotal about a first fixed pivot that is fixed relative to the first clamp jaw. The clamp assembly further comprises a linear driver comprising a linearly translating shaft. The clamp assembly further comprises a first linkage pivotal at one end about a second fixed pivot that is fixed relative to the first clamp jaw and coupled at an opposing end to the shaft at a first moving pivot. The clamp assembly further comprises a second linkage coupled at one end to the shaft at the first moving pivot, and coupled at the other end to the second clamp jaw at a second moving pivot. The linear driver is configured to linearly translate the shaft to apply force to the first moving pivot in a first direction to pivot the second clamp jaw towards the first clamp jaw, and to apply force to the first moving pivot in a second direction opposite to the first direction to pivot the second clamp jaw away from the first clamp jaw.

According to a third aspect, a system is provided. The system comprises a navigation tracker and a surgical attachment system for fixing the navigation tracker to a portion of bone. The surgical attachment system comprises an extension arm with a first end and a second end. An arm axis is defined between the first and second ends. The surgical attachment system further comprises an attachment interface at the first end of the extension arm and selectively coupled with the navigation tracker, and a clamp assembly disposed at the second end of the extension arm. The clamp assembly comprises a first clamp jaw comprising a first engagement surface and a second clamp jaw comprising a second engagement surface. The second clamp jaw faces the first clamp jaw and is pivotal about a first fixed pivot that is fixed relative to the first clamp jaw. The clamp assembly further comprises a linear driver comprising a linearly translating shaft. The clamp assembly further comprises a first linkage pivotal at one end about a second fixed pivot that is fixed relative to the first clamp jaw and coupled at an opposing end to the shaft at a first moving pivot. The clamp assembly further comprises a second linkage coupled at one end to the shaft at the first moving pivot, and coupled at the other end to the second clamp jaw at a second moving pivot. The linear driver is configured to linearly translate the shaft to apply force to the first moving pivot in a first direction to pivot the second clamp jaw towards the first clamp jaw, and to apply force to the first moving pivot in a second direction opposite to the first direction to pivot the second clamp jaw away from the first clamp jaw.

According to a fourth aspect, a navigation system is provided which includes a localizer for tracking the navigation tracker attached to the surgical attachment system of the third aspect.

Any of the above aspects can be utilized individually, or in combination.

Any of the above aspects can be utilized with any of the following implementations:

In one implementation, the second clamp jaw is coupled to the first clamp jaw at the first fixed pivot. In one implementation, the first linkage is coupled to the first clamp jaw at the second fixed pivot.

In one implementation, the first clamp jaw comprises an engagement portion that presents the first engagement surface. In one implementation, the first clamp jaw comprises a frame portion that extends along a first axis between first and second frame ends, with the first frame end of the frame portion disposed proximate the second end of the extension arm, and with the engagement portion extending from the second frame end of the frame portion transverse, or substantially perpendicular, to the first axis. In one implementation, the second clamp jaw is coupled to the frame portion of the first clamp jaw at a first fixed pivot. In one implementation, the first linkage is coupled to the frame portion of the first clamp jaw at a second fixed pivot, with the second fixed pivot disposed between the first fixed pivot and the first frame end of the frame portion.

In one implementation, the shaft is disposed along a second axis that is substantially perpendicular to the first axis. In one implementation, the shaft of the linear driver is threaded in a screw configuration and the linear driver further comprises a sleeve that is correspondingly threaded to receive the shaft, wherein actuation of linear driver is facilitated by rotation of the shaft about the second axis. In one implementation, the shaft further comprises a drive head configured to be rotated by a driver bit for actuating the linear driver.

In one implementation, the first and second clamp jaws and the first and second linkages are arranged to form a four-bar linkage. In one implementation, the first linkage is configured as an input link of the four-bar linkage. In one implementation, the first and second engagement surfaces of the first and second clamp jaws are configured as teeth for piercing into and gripping the bone.

In one implementation, the first clamp jaw comprises a frame portion that extends along a first axis between first and second frame ends, with the first frame end of the frame portion disposed proximate the second end of the extension arm. In one implementation, the first axis is substantially parallel to the arm axis. In one implementation, the first clamp jaw comprises an engagement portion that presents the first engagement surface, with the engagement portion extending from the second frame end of the frame portion transverse, or substantially perpendicular, to the first axis.

In one implementation, the clamp assembly comprises a frame fixed to the second end of the extension arm, with each of the first clamp jaw and the linear driver coupled to the frame. In one implementation, the attachment interface comprises a connector for coupling to the navigation tracker and first and second rotational adjusters disposed between the extension arm and the connector, with the first rotational adjuster configured to selectively rotate the connector about the arm axis, and with the second rotational adjuster configured to selectively rotate the connector about an interface axis, perpendicular to the first axis. In one implementation, the first and second rotational adjusters each comprise a pair of opposing lock teeth, with the pair of opposing lock teeth configured to rotate relative to one another when spaced apart and rotatably lock when in engagement with one another.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Example Surgical System

Referring to the Figures, wherein like numerals indicate like or corresponding parts throughout the several views, a system 10 (hereinafter "system") is shown throughout.

Figure 1:
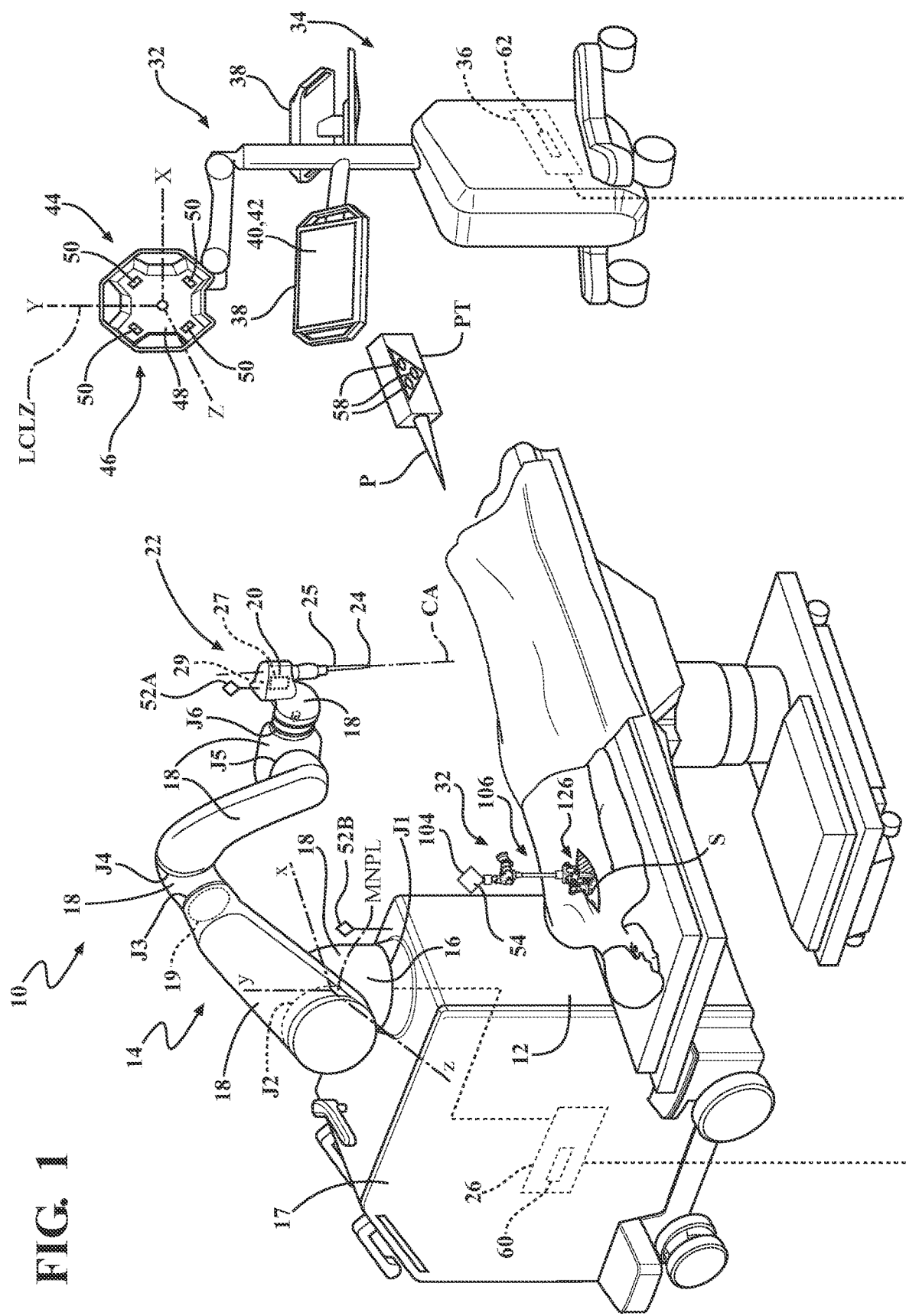
FIG. 1 is a perspective view of a robotic system for manipulating a target tissue of a patient with a tool, according to one example, including a surgical navigation system having a surgical attachment system and a navigation tracker.

As shown in FIG. 1, the system 10 may treat an anatomy (surgical site) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants, including unicompartmental, bicompartmental, multicompartmental, or total knee implants. Some of these types of implants are shown in U.S. Pat. No. 9,937,058, entitled, "Prosthetic Implant and Method of Implantation," the disclosure of which is hereby incorporated by reference. The system 10 and method disclosed herein may be used to perform other procedures, surgical or non-surgical, or may be used in industrial applications or other applications where robotic systems are utilized.

The system 10 may include a robotic manipulator 14. The robotic manipulator 14 has a base 16 and plurality of links 18. A manipulator cart 17 supports the robotic manipulator 14 such that the robotic manipulator 14 is fixed to the manipulator cart 17. The links 18 collectively form one or more arms of the robotic manipulator 14. The robotic manipulator 14 may have a serial arm configuration (as shown in FIG. 1) or a parallel arm configuration. In other examples, more than one robotic manipulator 14 may be utilized in a multiple arm configuration. The robotic manipulator 14 may comprise a plurality of (prismatic and/or rotating) joints (J) and a plurality of motor and/or joint encoders 19 located at the joints (J) for determining position data of the joints (J). For simplicity, only one joint encoder 19 is illustrated in FIG. 1, although it is to be appreciated that the other joint encoders 19 may be similarly illustrated. The robotic manipulator 14 according to one example has six joints (J1-J6) implementing at least six-degrees of freedom (DOF) for the robotic manipulator 14. However, the robotic manipulator 14 may have any number of degrees of freedom and may have any suitable number of joints (J) and redundant joints (J).

A surgical tool 20 (hereinafter "tool") couples to the robotic manipulator 14 and is movable relative to the base 16 to interact with the anatomy in certain modes. The tool 20 is or can form part of an end effector 22. The tool 20 may be grasped by the operator. One exemplary arrangement of the robotic manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The robotic manipulator 14 and the tool 20 may be arranged in alternative configurations. The tool 20 can be like that shown in U.S. Pat. No. 9,566,121, filed on Mar. 15, 2014, entitled, "End Effector of a Surgical Robotic Manipulator," hereby incorporated by reference.

The positioning of the end effector 22 and the tool 20 is defined by the robotic manipulator 14. This positioning may not be ideally suited for the ergonomics of an operator. To that end, the end effector 22 may include a handle 102 that is rotatable about a rotational axis R. The rotatable handle 102 allows the operator to hold the tool 20 in the most comfortable position while the robotic manipulator 14 moves the tool 20 into the necessary position for robotic manipulation. Exemplary arrangements of the handle 102 rotatable about the rotational axis R are described in U.S. Pat. No. 9,566,121, entitled, "End Effector of a Surgical Robotic Manipulator," and U.S. Patent Application Publication No. 2018/0110572, filed on Oct. 21, 2016, entitled, "Systems and Tools for Use with Surgical Robotic Manipulators," the disclosures of which are hereby incorporated by reference.

The tool 20 includes an energy applicator 24 designed to contact the target site, such as the tissue of the patient 12 at the surgical site. The energy applicator 24 may be a drill, a saw blade, a bur, an ultrasonic vibrating tip, or the like.

The system 10 includes a controller 30. The controller 30 includes software and/or hardware for controlling the robotic manipulator 14. The controller 30 directs the motion of the robotic manipulator 14 and controls a state (position and/or orientation) of the tool 20 with respect to a coordinate system of the manipulator 14.

As shown in FIG. 1, the system 10 further includes a surgical navigation system 32. One example of the surgical navigation system 32 is described in U.S. Pat. No. 9,008,757, filed on Sep. 24, 2013, entitled, "Navigation System Including Optical and Non-Optical Sensors," hereby incorporated by reference. The surgical navigation system 32 is configured to track movement of various objects. Such objects include, for example, the robotic manipulator 14, the tool 20 and the anatomy, e.g., scapula S. The surgical navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

The surgical navigation system 32 includes a cart assembly 34 that houses a navigation computer 36, and/or other types of control units. A navigation interface is in operative communication with the navigation computer 36. The navigation interface includes one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The surgical navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The surgical navigation system 32 includes one or more trackers. In one example, the trackers include a pointer tracker PT, one or more manipulator trackers 52, and a patient tracker 54. In the illustrated example of FIG. 1, the manipulator tracker 52 is firmly attached to the tool 20 (i.e., tracker 52A) and the patient tracker 54 is firmly affixed to the scapula S of the patient 12. In this example, the patient tracker 54 is firmly affixed to sections of bone. The pointer tracker PT is firmly affixed to a pointer P used for registering the anatomy to the localizer coordinate system LCLZ. The manipulator tracker 52 may be affixed to any suitable component of the robotic manipulator 14, in addition to, or other than the tool 20, such as the base 16 (i.e., tracker 52B), or any one or more links 18 of the robotic manipulator 14. The trackers 52, 54, PT may be fixed to their respective components in any suitable manner.

Any one or more of the trackers may include active markers 58. The active markers 58 may include light emitting diodes (LEDs). Alternatively, the trackers 52, 54 may have passive markers, such as reflectors, which reflect light emitted from the camera unit 46. Other suitable markers not specifically described herein may be utilized.

The localizer 44 tracks the trackers 52, 54 to determine a state of each of the trackers 52, 54 which correspond respectively to the state of the object respectively attached thereto. The localizer 44 provides the state of the trackers 52, 54 to the navigation computer 36. In one example, the navigation computer 36 determines and communicates the state the trackers 52, 54 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the surgical navigation system 32 is shown in the Figures, the surgical navigation system 32 may have any other suitable configuration for tracking the robotic manipulator 14 and the patient 12. In one example, the surgical navigation system 32 and/or localizer 44 are ultrasound-based. In another example, the surgical navigation system 32 and/or localizer 44 are radio frequency (RF)-based. In another example, the surgical navigation system 32 and/or localizer 44 are machine-vision based. The navigation system 32 can utilized any combination of these modalities.

The surgical navigation system 32 and/or localizer 44 may have any other suitable components or structure not specifically recited herein. Furthermore, any of the techniques, methods, and/or components described above with respect to the camera-based surgical navigation system 32 shown throughout the Figures may be implemented or provided for any of the other examples of the surgical navigation system 32 described herein. For example, the surgical navigation system 32 may utilize solely inertial tracking or any combination of tracking techniques.

The controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the robotic manipulator 14. In one example, as shown in FIG. 1, the manipulator controller is implemented on the manipulator computer 26. The manipulator controller 60 may receive and process data from a single source or multiple sources. The controller 30 further includes a navigation controller 62 for communicating the state data relating to the femur F, tibia T, and robotic manipulator 14 to the manipulator controller 60. The manipulator controller 60 receives and processes the state data provided by the navigation controller 62 to direct movement of the robotic manipulator 14. In one example, as shown in FIG. 1, the navigation controller 62 is implemented on the navigation computer 36. The manipulator controller 60 or navigation controller 62 may also communicate states of the patient 12 and robotic manipulator 14 to the operator by displaying an image of the femur F and/or tibia T and the robotic manipulator 14 on the one or more displays 38. The manipulator computer 26 or navigation computer 36 may also command display of instructions or request information using the display 38 to interact with the operator and for directing the robotic manipulator 14.

The robotic system shown in FIG. 1 is provided only as one possible example of a system that can be utilized with the clamping and attachment system described in the next section. The clamping and attachment system can be utilized with any type of navigated surgical system, such as one including manual hand-held tools, robotic hand-held tools, imaging systems (e.g., CT, X-ray, C-arms, etc.), or and for any type of navigated orthopedic or non-orthopedic procedure.

II. Surgical Clamping and Attachment System

Referring to the Figures, wherein like numerals indicate like or corresponding parts throughout the several views, the surgical navigation system 32 comprises a navigation tracker 104 is shown in FIG. 1. The navigation tracker 104 is utilized as the patient tracker described above, with the navigation computer 36 determining and communicating the state of the navigation tracker 104 to the manipulator computer 26. The navigation tracker 104 can have various configurations depending on the tracking modalities described above. One example of a navigation tracker that can be utilized with the navigation system 32 can be like that found in U.S. Pat. No. 10,537,395, entitled "Navigation Tracker with Kinematic Connector Assembly" the entire disclosure of which is hereby incorporated by reference.

The surgical navigation system 32 further comprises a surgical attachment system 106 for fixing the navigation tracker 104 to a portion of bone. As will become apparent from description below, the surgical attachment system 106 is configured to be selectively connected to and disconnected from the bone. As described above, the bone is the scapula S, which is beneficial for shoulder surgery. In one example, the bone portion is a coracoid process. However, the surgical attachment system 106 may be configured to fixed to any suitable bone, such as a femur, tibia, pelvis, or any part of the spinal bone (vertebra or spinous process).

The surgical attachment system 106 comprises an extension arm 108 with a first end 110 and a second end 112. An arm axis X is defined between the first and second ends 110, 112. As shown in FIGS. 2-6, the extension arm 108 may have a substantially cylindrical configuration. Said differently, the extension arm 108 may be configured as an elongated rod. However, the extension arm 108 may have any suitable configuration for supporting the navigation tracker 104 at a position spaced from the patient. The extension arm 108 can have any suitable length to enable the navigation tracker 104 to be exposed relative to the surgical site, and hence, trackable by the navigation system 32. In one example, the length of the extension arm 108 is in a range between 50-300 mm.

The surgical attachment system 106 further comprises an attachment interface 114 at the first end 110 of the extension arm 108 and selectively coupled with the navigation tracker 104. In the example shown in FIGS. 2-6, the attachment interface 114 comprises a connector 116 for coupling to the navigation tracker 104 and first and second rotational adjusters 118, 120 disposed between the extension arm 108 and the connector 116.

The connector 116 shown in FIGS. 2-6 is configured as a quick-connect coupler. More specifically, the quick-connect coupler corresponds with a connector on the navigation tracker 104. Coupling the navigation tracker 104 to the quick-connect coupler is performed by pushing the connector of the navigation tracker 104 onto the quick-connect coupler until the connector no longer moves on the quick-connect coupler. The connector on the navigation tracker 104 may be actuated (e.g., by sliding a collar) to remove the navigation tracker 104 from the attachment interface 114. Although the connector 116 of the attachment interface 114 is shown as a quick-connect coupler, the connector 116 may be configured in any other suitable configuration for coupling the navigation tracker 104 to the attachment interface 114 (e.g., threaded engagement). One example of such quick-connect couplers for a navigation tracker can be like that found in U.S. Pat. No. 10,537,395, entitled "Navigation Tracker with Kinematic Connector Assembly" the entire disclosure of which is hereby incorporated by reference.

Figure 5:
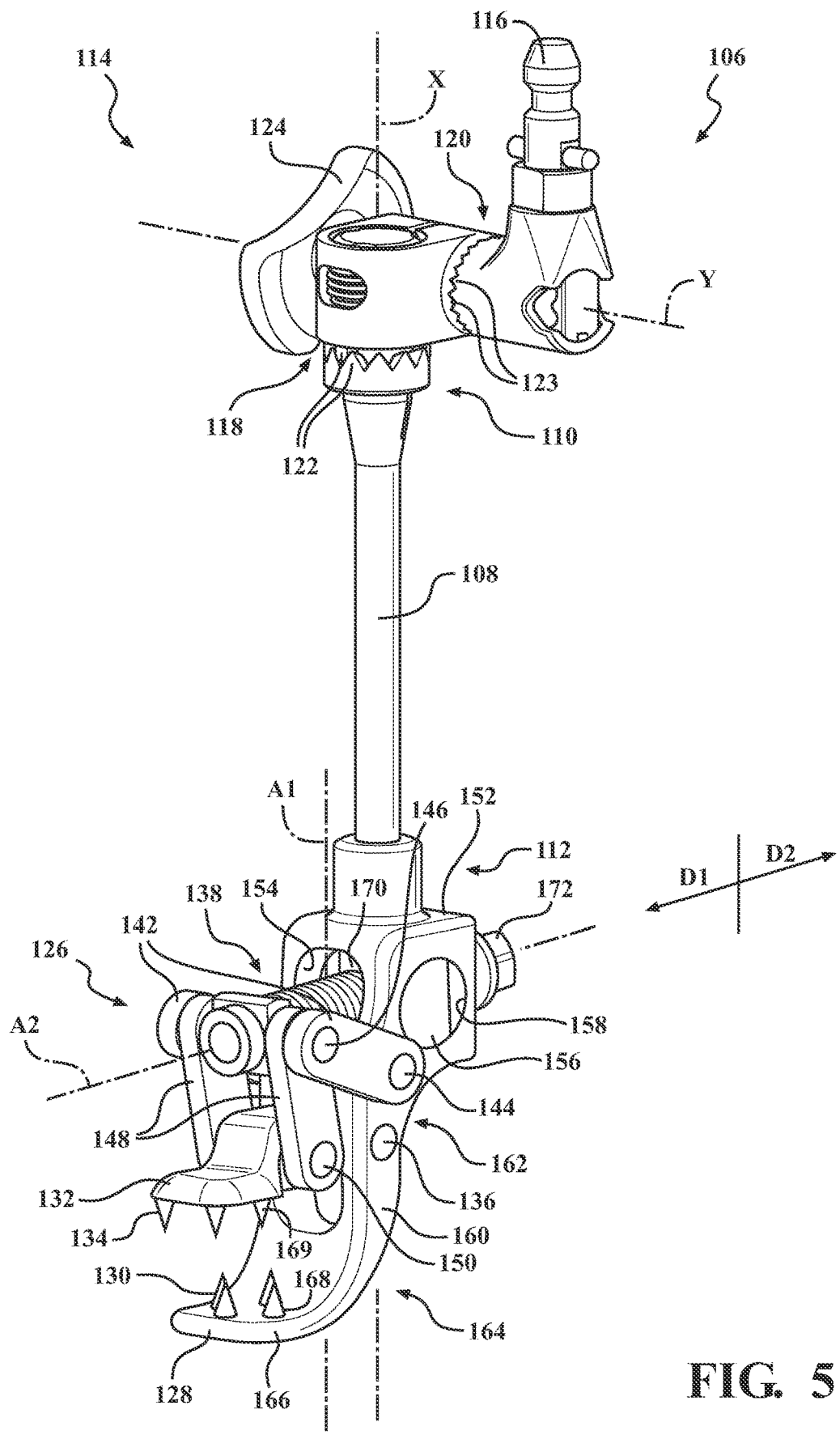
FIG. 5 is a perspective view of the surgical attachment system of FIG. 1, showing an attachment interface with a connector disposed in a vertical position.
Figure 6:
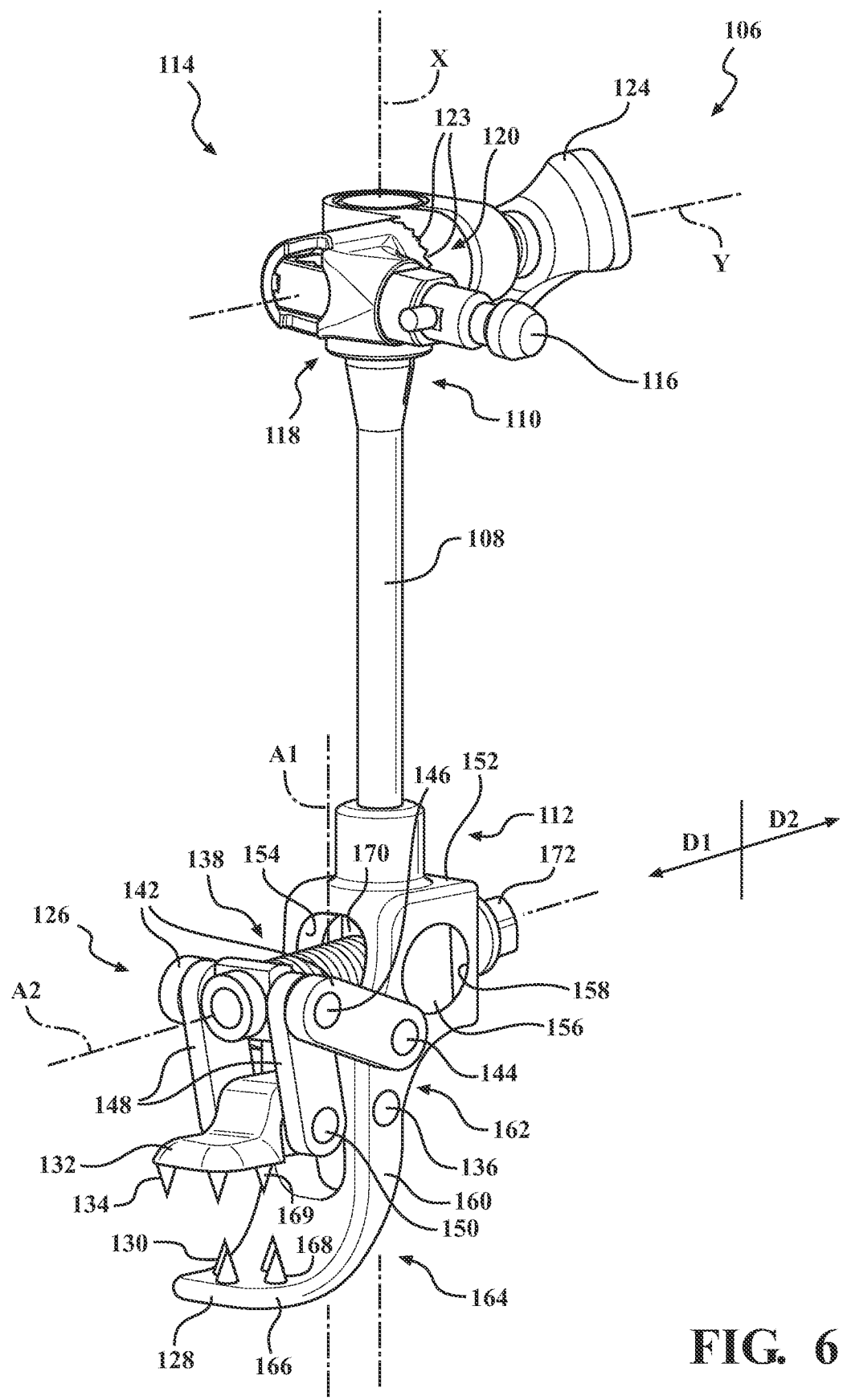
FIG. 6 is a perspective view of the surgical attachment system of FIG. 1, showing the attachment interface with the connector disposed in a horizontal position.

As shown between FIGS. 5 and 6, the first rotational adjuster 118 is configured to selectively rotate the connector 116 about the arm axis X, and with the second rotational adjuster 120 configured to selectively rotate the connector 116 about an interface axis Y, perpendicular to the arm axis X. Said differently, the first and second rotational adjusters 118, 120 allow for the selective adjustment of the navigation tracker 104 about two degrees of freedom. Furthermore, the first and second rotational adjusters 118, 120 are configured to selectively maintain the navigation tracker 104 in a desired position for allowing the navigation computer 36 to determine and communicate the state of the navigation tracker 104 to the manipulator computer 26 (i.e., by locking the first and second rotational adjusters 118, 120 and preventing rotation about the arm and interface axes X, Y).

In the example shown in FIGS. 5 and 6, the first and second rotational adjusters 118, 120 each comprise a pair of opposing lock teeth 122, 123, with the pair of opposing lock teeth 122, 123 configured to rotate relative to one another when spaced apart and rotatably lock when in engagement with one another. More specifically, as shown in FIGS. 5 and 6, the attachment interface 114 further comprises a knob 124. The knob 124 is operably coupled to each of the first and second rotational adjusters 118, 120. More specifically, rotating the knob 124 changes the spacing between the opposing lock teeth 122, 123. For example, rotating the knob 124 in a counter-clockwise direction (i.e., loosening the knob 124) moves apart the opposing lock teeth 122, 123 of each of the first and second rotational adjusters 118, 120. When the opposing lock teeth 122, 123 are spaced sufficiently apart, the teeth 122, 123 may rotate relative to one another about the respective arm and interface axes X, Y thus allowing the rotation of the first and second rotational adjusters 118, 120 about the axes X, Y. On the other hand, rotating the knob 124 in a clockwise direction (i.e., tightening the knob 124) moves together the opposing lock teeth 122, 123 of each of the first and second rotational adjusters 118, 120. When the opposing lock teeth 122, 123 contact one another (with opposing lock teeth 122, 123 alternating side-by-side about the respective arm and interface axes X, Y), the teeth 122, 123 may not rotate relative to one another about respective arm and interface axes X, Y thus locking rotation of the first and second rotational adjusters 118, 120 about the axes X, Y.

One example of the attachment interface 114 is shown in the Figures. However, the attachment interface 114 may utilize suitable configuration for allowing selective rotation of the navigation interface about the axes X, Y.

As shown in FIGS. 2-6, the surgical attachment system 106 further comprises a clamp assembly 126 disposed at the second end 112 of the extension arm 108. The clamp assembly 126 is used with the surgical attachment system 106 for fixing the navigation tracker 104 to the portion of the bone (as described above).

The surgical attachment system 106 and clamp assembly 126 described herein have several advantages. The clamp assembly 126 has a large throw size (range of motion) and is sized to fit 90% or greater of coracoid sizes which provides a wide applicability to surgical procedures without requiring different clamps for different sized patients. The surgical attachment system 106 and clamp assembly 126 also exhibit a small footprint in the working area of a surgical site, which is particularly advantageous for a shoulder replacement surgery wherein there is limited incision size and surgeon access to the surgical site. The surgical attachment system 106 and clamp assembly 126 do not obstruct the surgeon's access to the glenoid for bone preparation. To provide increased flexibility and to further reduce footprint, the surgical attachment system 106 has a two degree of freedom mechanism at the top of the clamp that enables the navigation tracker 104 to be pointed towards the localizer 44. This enables the surgical attachment system 106 and clamp assembly 126 to be utilized in tight spaces and at difficult surgical access angles while providing the ability of the navigation tracker 104 to maintain line-of-sight to the localizer 44. The small footprint of the surgical attachment system 106 and clamp assembly 126 further enable unobstructed post joint-reduction range of motion assessment. Other advantages can be understood from the detailed description and drawings.

The clamp assembly 126 comprises a first clamp jaw 128 comprising a first engagement surface 130 and a second clamp jaw 132 comprising a second engagement surface 134. The second clamp jaw 132 faces the first clamp jaw 128 and is pivotal about a first fixed pivot 136 that is fixed relative to the first clamp jaw 128. Although the clamp assembly 126 is shown in the example to comprise the two clamp jaws 128, 132, the clamp assembly 126 may be configured to comprise any number of clamp jaws.

The clamp assembly 126 further comprises a linear driver 138 comprising a linearly translating shaft 140. The shaft 140 of the linear driver 138 may be disposed along a second axis A2. The clamp assembly 126 further comprises a first linkage 142. The first linkage 142 is pivotal at one end about a second fixed pivot 144 that is fixed relative to the first clamp jaw 128 and is coupled at an opposing end to the shaft 140 at a first moving pivot 146. The clamp assembly 126 further comprises a second linkage 148 coupled at one end to the shaft 140 and the opposing end of the first linkage 142 at the first moving pivot 146. The second linkage 148 is coupled at the other end to the opposing end of the second clamp jaw 132 at a second moving pivot 150.

Figure 3:
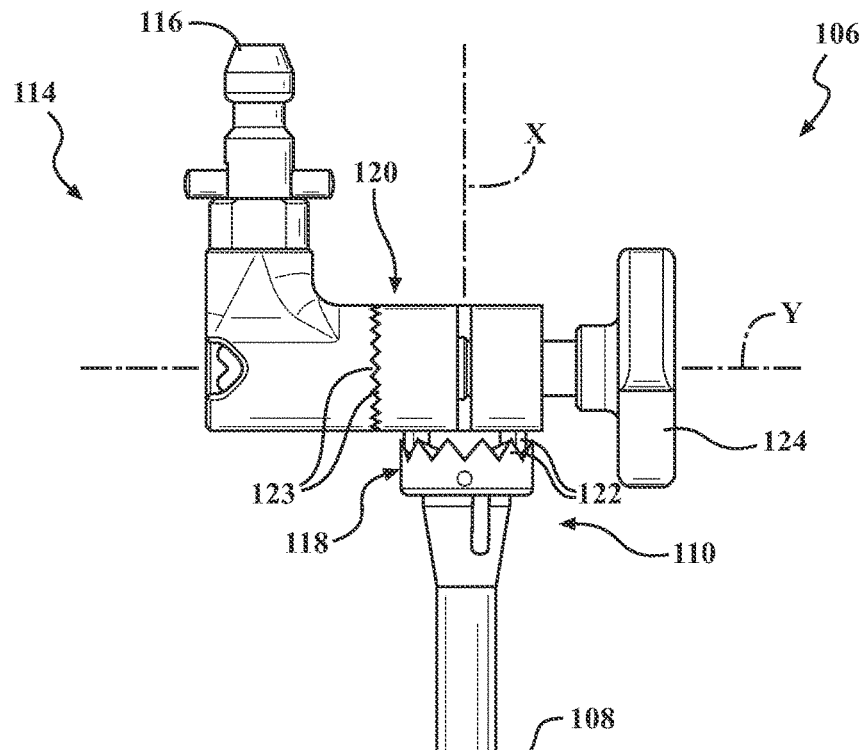
FIG. 3 is an elevational view of the surgical attachment system of FIG. 1, showing a first clamp jaw having a first engagement surface and a second clamp jaw having a second engagement surface, with the first and second engagement surfaces in an open position.
Figure 3:
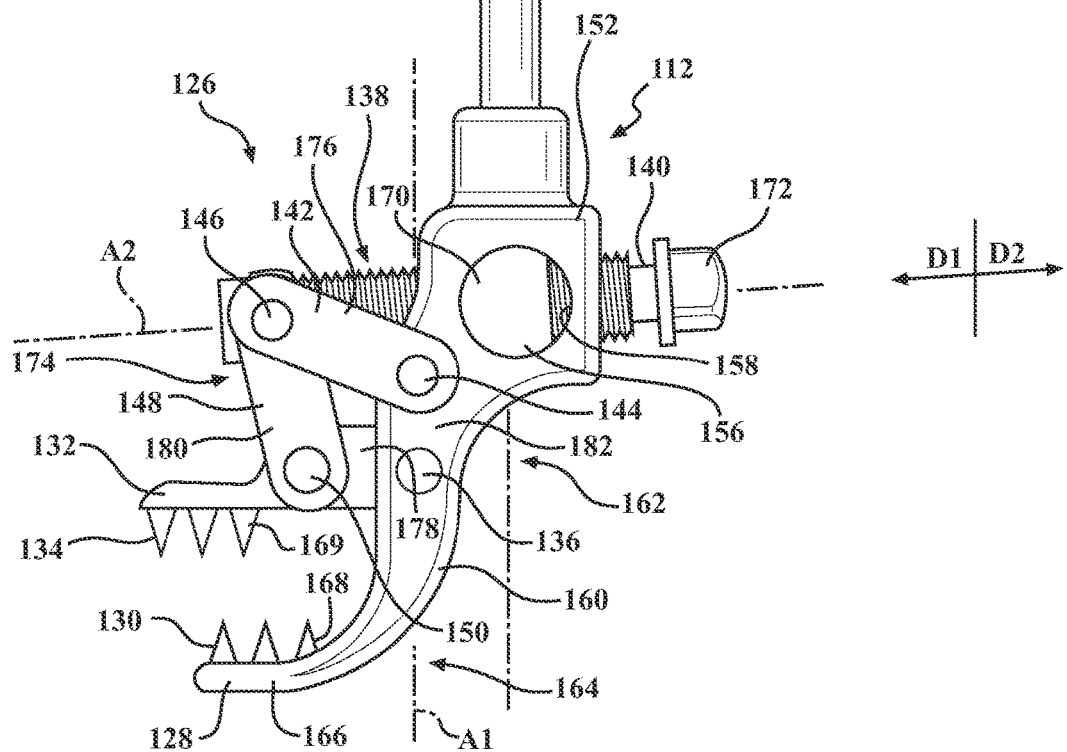
Figure 4:
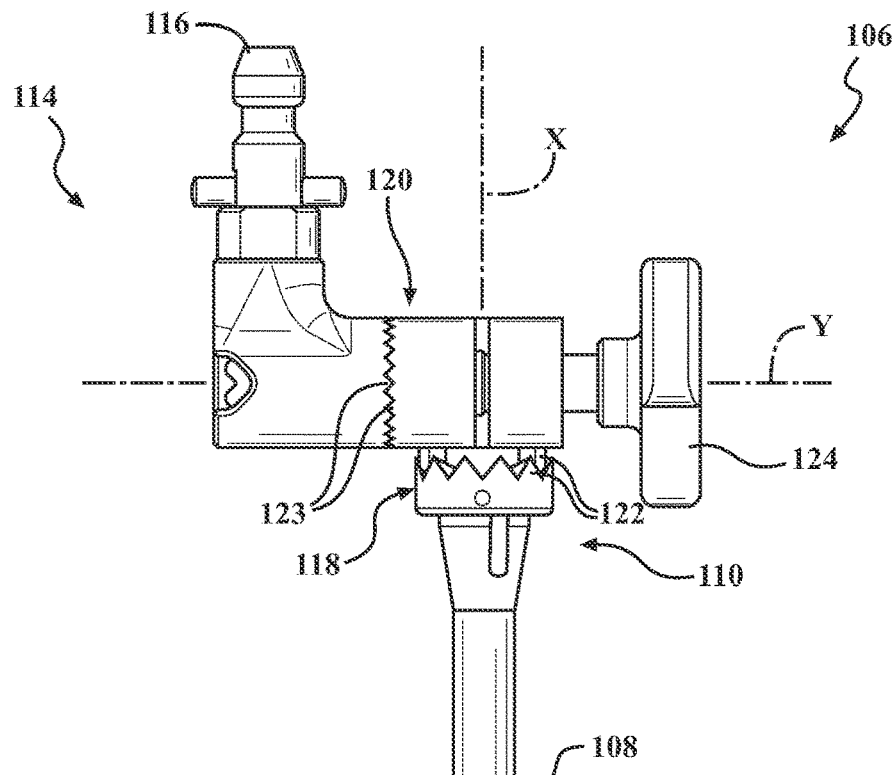
FIG. 4 is an elevational view of the surgical attachment system of FIG. 1, with the first and second engagement surfaces in a closed position.
Figure 4:
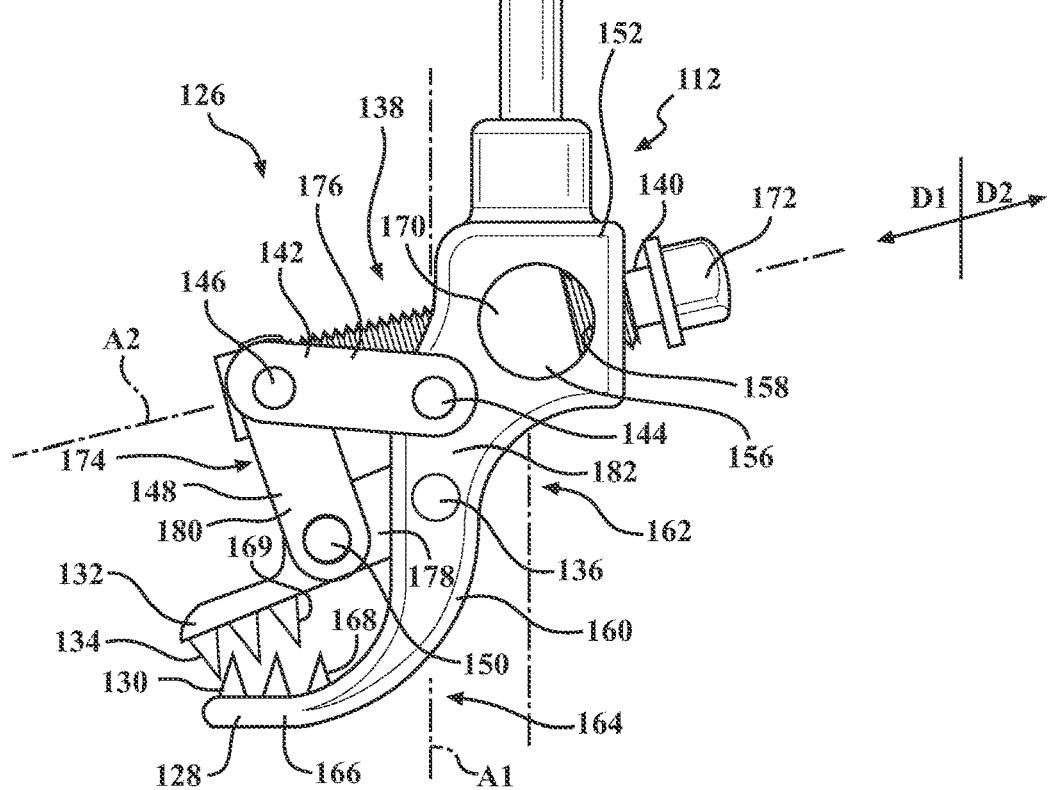

With reference to FIGS. 3 and 4, the linear driver 138, when actuated, is configured to linearly translate the shaft 140 to apply force to the first moving pivot 146 in a first direction D1 to pivot the second clamp jaw 132 towards the first clamp jaw 128. Likewise, the linear driver 138 is configured to apply force to the first moving pivot 146 in a second direction D2, opposite to the first direction D1, to pivot the second clamp jaw 132 away from the first clamp jaw 128.

Accordingly, linear translation of the shaft 140 of the linear driver 138 is converted into rotational motion of the second clamp jaw 132 about the first fixed pivot 136. The conversion is facilitated through the interactions between the first and second clamp jaws 128, 132 and the first and second linkages 142, 148 through the first and second fixed pivots 136, 144 and the first and second moving pivots 146, 150.

Furthermore, the utilization of the first and second moving pivots 146, 150 and the first and second fixed pivots 136, 144 reduces the volume and length of the clamp assembly 126. More specifically, other "scissor-like" clamps have two jaws pivotal about one fixed pivot, which require greater length to achieve the required leverage on the jaws to firmly attach the clamp assembly 126 to the bone of the patient. The reduction in volume and length provides improved post joint-reduction range of motion assessment. The reduction in volume and length also aides in clamping anatomy through limited surgical access angle or direction, e.g., such as clamping the scapula S. Moreover, the first and second moving pivots 146, 150 and the first and second fixed pivots 136, 144 allow the utilization of the linear driver 138 coupled to the first moving point, which further reduces the volume and length of the clamp assembly 126.

As shown in FIGS. 2-6, the clamp assembly 126 may comprise a frame 152 fixed to the second end 112 of the extension arm 108, with each of the first clamp jaw 128 and the linear driver 138 coupled to the frame 152. In the example shown in the Figures, the first clamp jaw 128 is integrally formed with the frame 152 such that the first clamp jaw 128 and the frame 152 are configured as a single unit. However, the first clamp jaw 128 may be coupled to the frame 152 in any suitable manner, including (but not limited to) welding, chemical adhesion, and mechanical fastening.

Figure 2:
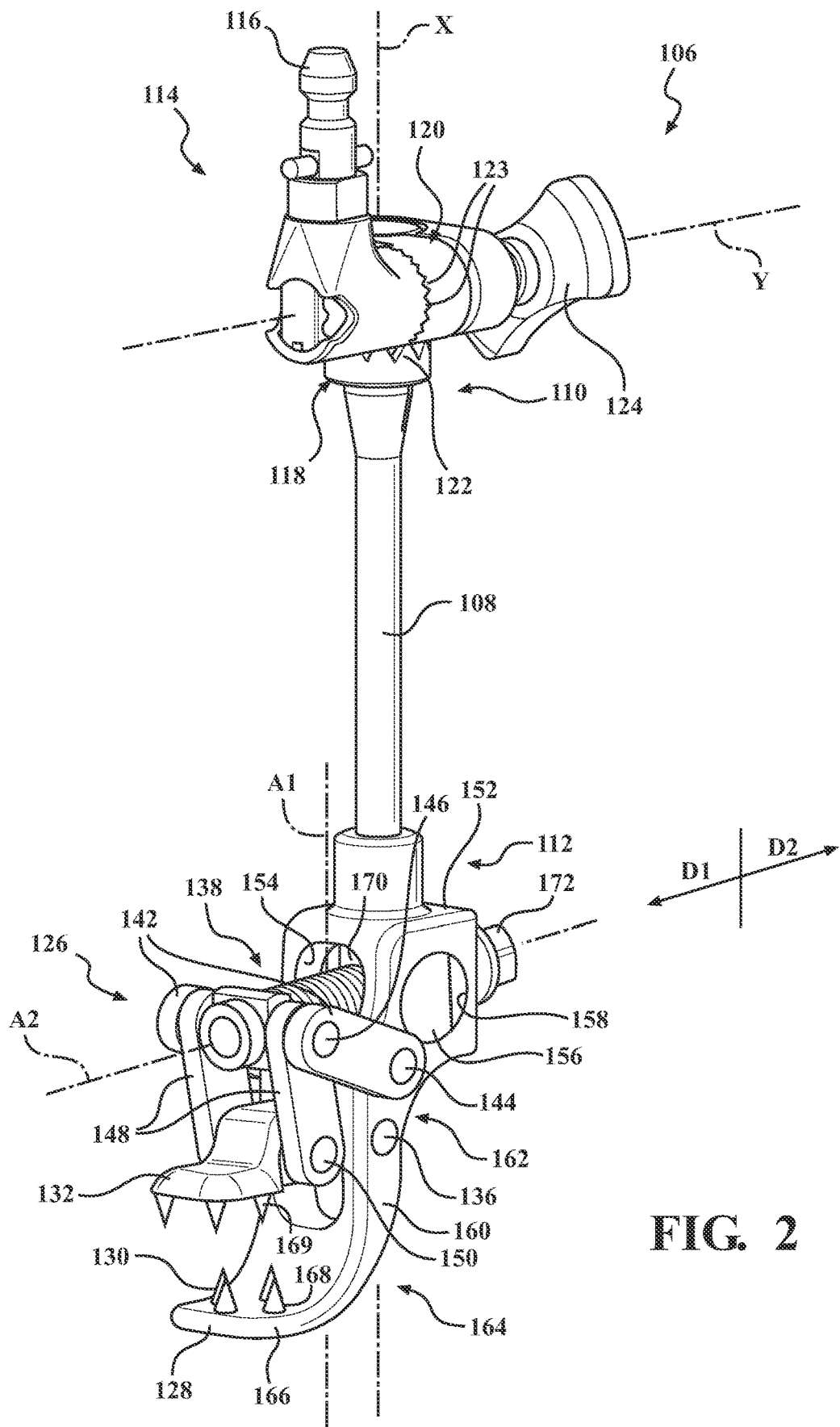
FIG. 2 is a perspective view of the surgical attachment system of FIG. 1.

The frame 152 may optionally define an aperture 154 with the linear driver 138 at least partially disposed within the aperture 154, as shown in FIGS. 2, 5, and 6. However, the linear driver 138 may be disposed entirely outside the frame 152. Furthermore, the linear driver 138 may include a pair of posts 156 opposing one another and the frame 152 may define a pair of holes 158 configured to receive the posts 156. The posts 156 and the holes 158 are sized and shaped such that the linear driver 138 is retained within the holes 158 and is configured to pivot or tilt about an axis defined by the holes 158 (the axis being in and out of the page of the Figure). As such, the linear driver 138 may pivot relative to the frame 152 at the posts 156. In other words, the axis A2 of the shaft 140 can positioned relative to the arm axis X in one position (e.g., substantially perpendicular) when the clamp is open as shown in FIG. 3, and positioned relative to the arm axis X in another position (e.g., at angle greater than 100 degrees) when the clamp is closed as shown in FIG. 4. Depending on the configuration or length of the shaft 140 and linkages 142, 148, the degree of tilting of the linear driver 138 relative to the arm axis X can be greater than or less than that shown in the Figures. Pivoting of the linear driver 138 facilitates pivoting of the second clamp jaw 132 when the shaft 140 translates because the shaft 140 is coupled to the first and second linkages 142, 148 at the first moving pivot 146. The pivoting of the linear driver 138 allows the first moving pivot 146 to move as the shaft 140 translates. In the example shown in the Figures, the linear driver 138 generally pivots between an angle of approximately 90 degrees between the axis A2 and the arm axis X and an angle of approximately 75 degrees between the axis A2 and arm axis X. However, in other examples the angle may vary depending on the size and shape of the anatomy to which the clamp assembly 126 will be affixed.

As shown in FIGS. 2, 5, and 6, the first linkage 142 may be further defined as a pair of first linkages 142 disposed on opposing sides of the frame 152 with the linear driver 138 disposed therebetween. Likewise, the second linkage 148 may be further defined as a pair of second linkages 148 disposed on opposing sides of the frame 152 with the linear driver 138 disposed therebetween. The pair of first linkages 142 and the pair of second linkages 148 are identical mirror images of one another and support opposing sides of the second clamp jaw 132. One having skill in the art will appreciate that any number of first and second linkages 142, 148 may be utilized. The first and second linkages 142, 148 are described below in greater detail as singular components. However, because the pair of first linkages 142 and the pair of second linkages 148 are identical mirror images of one another, the description below is applicable to both of the pair of first linkages 142 and both of the pair of second linkages 148.

As shown in FIGS. 3 and 4, the first clamp jaw 128 may comprise a frame portion 160 that extends along a first axis A1 between first and second frame ends 162, 164. In some instances, the first axis A1 is substantially parallel to the arm axis X. The first frame end 162 of the frame portion 160 is disposed proximate the second end 112 of the extension arm 108. The first clamp jaw 128 comprises an engagement portion 166 that presents the first engagement surface 130. The engagement portion 166 extends from the second frame end 164 of the frame portion 160 transverse, or substantially perpendicular, to the first axis A1. As such, the first clamp jaw 128 may have a substantially L-shape, curved L, or J-shape configuration. The second clamp jaw 132 may be coupled to the first clamp jaw 128 at the first fixed pivot 136. More specifically, the second clamp jaw 132 may be coupled to the frame portion 160 of the first clamp jaw 128 at the first fixed pivot 136. As such, the length of the frame portion 160 is configured to space apart the engagement portion 166 of the first clamp jaw 128 from the second clamp jaw 132. In doing so, the clamp jaws are configured to grasp bones of a particular range of thickness. In this example, the length of the frame portion 160 is sized to accommodate a scapula S or other bones of similar thickness. More specifically, in this example, the clamp assembly 126 is sized to accommodate a bone having a thickness of up to 15 mm. However, the length of the frame portion 160 may be changed to accommodate bones of different thicknesses.

The first and second engagement surfaces 130, 134 of the first and second clamp jaws 128, 132 may be configured as teeth 168, 169 for piercing into and gripping the bone. As shown in FIGS. 2, 5, and 6, the teeth 168, 169 have a conical configuration. However, the teeth 168, 169 may have any suitable configuration for piercing into the bone. Moreover, in other examples the first and second engagement surfaces 130, 134 may have configurations other than teeth 168, 169 configured to fix the clamp assembly 126 to the bone. For example, the first and second engagement surfaces 130, 134 may have an abrasive texture that increases the coefficient of friction between the bone and the first and second engagement surfaces 130, 134 when in contact with the bone. The first and second engagement surfaces 130, 134 may have any suitable configuration for fixing the clamp assembly 126 to the bone.

As described above, the linear driver 138 may pivot relative to the frame 152. Therefore, the second axis A2 of the shaft 140 may pivot relative to the first axis A1 of the frame portion 160. As shown in FIGS. 3 and 4, the axis A2 of the shaft 140 can positioned relative to the first axis A1 of the frame portion 160 in one position (e.g., substantially perpendicular) when the clamp is open as shown in FIG. 3, and positioned relative to the first axis A1 of the frame portion 160 in another position (e.g., at angle less than 80 degrees) when the clamp is closed as shown in FIG. 4. The degree of pivoting between the first and second axes A1, A2 is not limited strictly to the configuration shown in the Figures and can vary depending on the configuration or length of the shaft 140, linkages 142, 148, frame 152, and the like.

The shaft 140 of the linear driver 138 may be threaded in a screw configuration. The linear driver 138 may further comprise a threaded nut 170 that is correspondingly threaded to receive the shaft 140. Actuation of the linear driver 138 is facilitated by rotation of the shaft 140 about the second axis A2. The posts 156 described above may be fixed to the threaded nut 170. As such, the threaded nut 170 remains positioned relative to the frame 152 when the shaft 140 is rotated. Thus, the shaft 140 moves relative to the threaded nut 170 and the frame 152. Rotation of the shaft 140 about the second axis A2 in a first rotational direction (commonly a clockwise direction) causes the linear driver 138 to extend (i.e., the shaft 140 moves the first moving pivot 146 in the first direction D1 away from the frame 152 and move the second clamp jaw 132 toward the first clamp jaw 128). Rotation of the shaft 140 about the second axis A2 in a second rotational direction (commonly a counter-clockwise direction) causes the linear driver 138 to contract (i.e., the shaft 140 moves the first moving pivot 146 in the second direction D2 toward the frame 152 and move the second clamp jaw 132 away from the first clamp jaw 128).

The shaft 140 may further comprise a drive head 172 configured to be rotated by a driver bit for actuating the linear driver 138. In the example shown in FIGS. 3 and 4, the drive head 172 is configured as a square head that can be driven by a corresponding driver bit. However, the driver head may be any suitable size and shape. Furthermore, the driver bit can be coupled to a powered hand tool or a non-powered (manually driven) hand tool.

In the example shown in the Figures, the first and second clamp jaws 128, 132, the first and second linkages 142, 148, and the linear driver 138 are planarly aligned. More specifically, each of the first and second fixed pivots 136, 144 and the first and second moving pivots 146, 150 are configured as pins that extend parallel to one another and allow for rotation about one degree of freedom. As such, the first and second clamp jaws 128, 132, the first and second linkages 142, 148, and the linear driver 138 are configured to move in two degrees of freedom. As shown in FIGS. 3 and 4, the first linkage 142 is coupled to the first clamp jaw 128 at the second fixed pivot 144. The first linkage 142 is coupled to the frame portion 160 of the first clamp jaw 128 at the second fixed pivot 144, with the second fixed pivot 144 disposed between the first fixed pivot 136 and the first frame end 162 of the frame portion 160. As such, the first and second clamp jaws 128, 132 and the first and second linkages 142, 148 are arranged to form a four-bar linkage 174 (i.e., a movable closed-chain linkage). More specifically, the frame portion 160 of the first clamp jaw 128 (between the first and second fixed pivots 136, 144), the second clamp jaw 132, and the first and second linkages 142, 148 are arranged to form the four-bar linkage 174.

In the example shown in the Figures, the first linkage 142 is configured as an input link 176 of the four-bar linkage 174. The second clamp jaw 132 is configured as an output link 178 of the four-bar linkage 174. The second linkage 148 is configured as a floating link 180 of the four-bar linkage 174. The frame portion 160 of the first clamp jaw 128 (between the first and second fixed pivots 136, 144) is configured as a ground link 182 of the four-bar linkage 174.

The four-bar linkage 174 shown in the Figures is further defined as a Grashof condition four-bar linkage 174, with the input and output links 176, 178 (i.e., the first linkage 142 and the second clamp jaw 132) both characterized as cranks. A crank refers to an input link 176 and/or an output link 178 that is capable of completely rotating about the respective fixed pivot (i.e., 360 degrees of rotation). This condition is dictated by the lengths of the links. More specifically, at least one of the input and output links 176, 178 is a crank when the sum of the lengths of the shortest and longest links is less than the sum of the lengths of the other two links.

As shown in FIGS. 3 and 4, the frame portion 160 of the first clamp jaw 128 (between the first and second fixed pivots 136, 144) is the shortest link. The first and second linkages 142, 148 are equal length and are both equally considered the longest link. The second jaw clamp is an intermediate length between the shortest and longest links. Accordingly, the sum of the lengths of the frame portion 160 of the first clamp jaw 128 and one of the first and second linkages 142, 148 is less than the sum of the lengths of the other one of the first and second linkages 142, 148 and the second clamp jaw 132. A Grashof condition four-bar linkage with the input and output links both characterized as cranks is also referred to as a drag-link four-bar linkage.

The advantage of a drag-link four-bar linkage is the range of motion of both the input and output links 176, 178. Because the output link 178 is capable of full rotation, the first and second clamp jaws 128, 132 are capable of accommodating a wider range of bone thicknesses. Likewise, because the input link 176 is capable of full rotation, the shaft 140 of the linear driver 138 can be linearly translated a greater amount allowing for fine tuning of the position of the first linkage 142 and the second clamp jaw 132. Therefore, a user may precisely adjust the position of the second clamp jaw 132 to ensure proper fixation of the clamp assembly 126 to the bone, while reducing the possibility for overtightening the clamp assembly 126 and damaging the bone and/or the clamp assembly 126.

Although both the first linkage 142 and the second clamp jaw 132 are theoretically capable of complete rotation about the first and second fixed pivots 136, 144, respectively, the range of motion of the first linkage 142 and the second clamp jaw 132 may be limited due to contact with other components in the examples shown in the Figures. With reference to FIGS. 2, 5, and 6, rotation of the second clamp jaw 132 away from the first clamp jaw 128 occurs until the second linkage 148 (more specifically, the pair of second linkages 148) contacts the frame 152. Likewise, rotation of the second clamp jaw 132 toward the first clamp jaw 128 occurs until the second clamp jaw 132 contacts the first clamp jaw 128 at the first and second engagement surfaces 130, 134.

Although the example in FIGS. 3 and 4, shows the first and second clamp jaws 128, 132 and the first and second linkages 142, 148 configured as a drag-link four-bar linkage, the first and second clamp jaws 128, 132 and the first and second linkages 142, 148 may be arranged in any suitable four-bar linkage configuration.

The operation of rotating the second clamp jaw 132 toward the first clamp jaw 128 in the example shown in FIGS. 2-6 will be discussed below for illustrative purposes only.

With the second clamp jaw 132 positioned relative to the first clamp jaw 128 as shown in FIG. 3, the user actuates the linear driver 138, causing the linear driver 138 to extend. More specifically, the user engages the drive head 172 and rotates of the shaft 140 about the second axis A2 in the first rotational direction causing the shaft 140 to move the first moving pivot 146 away from the frame 152 in the first direction D1. The shaft 140 rotates the first linkage 142 about the second fixed pivot 144, causing the first moving pivot 146 to move toward the first clamp jaw 128. In turn, the second linkage 148 (coupled to the first linkage 142 at the first moving pivot 146) also moves toward the first clamp jaw 128. The movement of the second linkage 148 toward the first clamp jaw 128 causes the second clamp jaw 132 (coupled to the second linkage 148 at the second moving pivot 150) to rotate about the first fixed pivot 136 toward the first clamp jaw 128. The first and second engagement surfaces 130, 134 of the first and second clamp jaws 128, 132, respectively, move toward one another. FIG. 4 shows an exemplary position of the clamp assembly 126 after the second clamp jaw 132 is rotated toward the first clamp jaw 128. The movement of the second clamp jaw 132 occurs during actuation of the linear driver 138 and is thus directly controlled by the user. When a bone is disposed between the first and second engagement surfaces 130, 134, the user actuates the linear driver 138 and moves the second engagement surface 134 toward the first engagement surface 130 until the first and second engagement surfaces 130, 134 contact the bone with sufficient pressure to ensure that the clamp assembly 126 is fixed to the bone.

The operation of rotating the second clamp jaw 132 away from the first clamp jaw 128 in the example shown in FIGS. 2-6 will be discussed below for illustrative purposes only.

With the second clamp jaw 132 positioned relative to the first clamp jaw 128 as shown in FIG. 4, the user actuates the linear driver 138, causing the linear driver 138 to contract. More specifically, the user engages the drive head 172 and rotates of the shaft 140 about the second axis A2 in the second rotational direction causing the shaft 140 to move the first moving pivot 146 toward the frame 152 in the second direction D2. The shaft 140 rotates the first linkage 142 about the second fixed pivot 144, causing the first moving pivot 146 to move away from the first clamp jaw 128. In turn, the second linkage 148 (coupled to the first linkage 142 at the first moving pivot 146) also moves away from the first clamp jaw 128. The movement of the second linkage 148 away from the first clamp jaw 128 causes the second clamp jaw 132 (coupled to the second linkage 148 at the second moving pivot 150) to rotate about the first fixed pivot 136 away from the first clamp jaw 128. The first and second engagement surfaces 130, 134 of the first and second clamp jaws 128, 132, respectively, move away from one another. FIG. 3 shows an exemplary position of the clamp assembly 126 after the second clamp jaw 132 is rotated away from the first clamp jaw 128. The movement of the second clamp jaw 132 occurs during actuation of the linear driver 138 and is thus directly controlled by the user. When a bone is disposed between the first and second engagement surfaces 130, 134, the user actuates the linear driver 138 and moves the second engagement surface 134 away from the first engagement surface 130 until the first and second engagement surfaces 130, 134 are spaced from the bone and the clamp assembly 126 may be removed from the bone.

Those skilled in the art can appreciate that the above clamping and attachment system can be designed with a configuration, look, or function that differs specifically from the implementation shown in the Figures. The scope of the invention is not limited exclusively to the Figures and may include equivalents to any components described herein which operate with a similar function and accomplish a similar result.

Several examples have been described in the foregoing description. However, the examples discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clamp assembly for use with a surgical attachment system for fixing a navigation tracker to a portion of bone, the clamp assembly comprising:
    a first clamp jaw comprising a first engagement surface;
    a second clamp jaw comprising a second engagement surface, wherein the second clamp jaw faces the first clamp jaw and is pivotal about a first fixed pivot that is fixed relative to the first clamp jaw;
    a linear driver comprising a shaft that is configured to linearly translate;
    a first linkage pivotal at one end about a second fixed pivot that is fixed relative to the first clamp jaw, and coupled at an opposing end to the shaft at a first moving pivot;
    a second linkage coupled at one end to the shaft at the first moving pivot, and coupled at an opposing end to the second clamp jaw at a second moving pivot; and
    wherein the linear driver is configured to linearly translate the shaft to apply force to the first moving pivot in a first direction to pivot the second clamp jaw towards the first clamp jaw, and to apply force to the first moving pivot in a second direction opposite to the first direction to pivot the second clamp jaw away from the first clamp jaw.

2. The clamp assembly as set forth in claim 1, wherein the second clamp jaw is coupled to the first clamp jaw at the first fixed pivot.

3. The clamp assembly as set forth in claim 1, wherein the first linkage is coupled to the first clamp jaw at the second fixed pivot.

4. The clamp assembly as set forth in claim 1, wherein the first clamp jaw comprises an engagement portion that presents the first engagement surface.

5. The clamp assembly as set forth in claim 4, wherein the first clamp jaw comprises a frame portion that extends along a first axis between first and second frame ends, and the first frame end of the frame portion is disposed proximate to an extension arm, and the engagement portion extends from the second frame end of the frame portion substantially perpendicular to the first axis.

6. The clamp assembly as set forth in claim 5, wherein the second clamp jaw is coupled to the frame portion of the first clamp jaw at the first fixed pivot.

7. The clamp assembly as set forth in claim 6, wherein the first linkage is coupled to the frame portion of the first clamp jaw at the second fixed pivot, and the second fixed pivot is disposed between the first fixed pivot and the first frame end of the frame portion.

8. The clamp assembly as set forth in claim 5, wherein the shaft is disposed along a second axis that is transverse to the first axis.

9. The clamp assembly as set forth in claim 8, wherein, in response to linearly translation of the shaft by the linear driver, the second axis of the shaft is configured to tilt relative to the first axis of the frame portion.

10. The clamp assembly as set forth in claim 8, wherein the shaft of the linear driver is threaded in a screw configuration and the linear driver further comprises a sleeve that is correspondingly threaded to receive the shaft, wherein actuation of linear driver is facilitated by rotation of the shaft about the second axis.

11. The clamp assembly as set forth in claim 1, wherein the shaft further comprises a drive head configured to be rotated by a driver bit for actuating the linear driver.

12. The clamp assembly as set forth in claim 1, wherein the first and second clamp jaws and the first and second linkages are arranged to form a four-bar linkage.

13. The clamp assembly as set forth in claim 1, wherein the first engagement surface and the second engagement surface are each configured as teeth for piercing into and gripping the portion of bone.

14. A surgical attachment system for fixing a navigation tracker to a portion of bone, the surgical attachment system comprising:
  an extension arm with a first end and a second end, an arm axis being defined between the first and second ends;
  an attachment interface at the first end of the extension arm and being configured to detachably couple to the navigation tracker; and
  a clamp assembly disposed at the second end of the extension arm and comprising:
    a first clamp jaw comprising a first engagement surface;
    a second clamp jaw comprising a second engagement surface, wherein the second clamp jaw faces the first clamp jaw and is pivotal about a first fixed pivot that is fixed relative to the first clamp jaw;
    a linear driver comprising a shaft that is configured to linearly translate;
    a first linkage pivotal at one end about a second fixed pivot that is fixed relative to the first clamp jaw, and coupled at an opposing end to the shaft at a first moving pivot;
    a second linkage coupled at one end to the shaft at the first moving pivot, and coupled at an opposing end to the second clamp jaw at a second moving pivot; and
    wherein the linear driver is configured to linearly translate the shaft to apply force to the first moving pivot in a first direction to pivot the second clamp jaw towards the first clamp jaw, and to apply force to the first moving pivot in a second direction opposite to the first direction to pivot the second clamp jaw away from the first clamp jaw.

15. The surgical attachment system as set forth in claim 14, wherein the first clamp jaw comprises a frame portion that extends along a first axis that is transverse to the arm axis, and that extends between first and second frame ends, and the first frame end of the frame portion is disposed proximate the second end of the extension arm.

16. The surgical attachment system as set forth in claim 15, wherein the first clamp jaw comprises an engagement portion that presents the first engagement surface, and the engagement portion extends from the second frame end of the frame portion and extends substantially perpendicular to the first axis.

17. The surgical attachment system as set forth in claim 14, wherein the clamp assembly comprises a frame fixed to the second end of the extension arm, and each of the first clamp jaw and the linear driver are coupled to the frame of the clamp assembly.

18. The surgical attachment system as set forth in claim 14, wherein the attachment interface comprises a connector for coupling to the navigation tracker and first and second rotational adjusters disposed between the extension arm and the connector, with the first rotational adjuster configured to selectively rotate the connector about the arm axis, and the second rotational adjuster is configured to selectively rotate the connector about an interface axis, perpendicular to the arm axis.

19. The surgical attachment system as set forth in claim 18, wherein the first and second rotational adjusters each comprise a pair of opposing lock teeth, with the pair of opposing lock teeth configured to rotate relative to one another when spaced apart and rotatably lock when in engagement with one another.

20. An assembly comprising:
  a navigation tracker; and
  a surgical attachment system for fixing the navigation tracker to a portion of bone, the surgical attachment system comprising:
    an extension arm with a first end and a second end, an arm axis being defined between the first and second ends;
    an attachment interface at the first end of the extension arm and coupled to the navigation tracker; and
    a clamp assembly disposed at the second end of the extension arm and comprising:
      a first clamp jaw comprising a first engagement surface;
      a second clamp jaw comprising a second engagement surface, wherein the second clamp jaw faces the first clamp jaw and is pivotal about a first fixed pivot that is fixed relative to the first clamp jaw;
      a linear driver comprising a shaft that is configured to linearly translate;
      a first linkage pivotal at one end about a second fixed pivot that is fixed relative to the first clamp jaw, and coupled at an opposing end to the shaft at a first moving pivot;
      a second linkage coupled at one end to the shaft at the first moving pivot, and coupled at an opposing end to the second clamp jaw at a second moving pivot; and
      wherein the linear driver is configured to linearly translate the shaft to apply force to the first moving pivot in a first direction to pivot the second clamp jaw towards the first clamp jaw, and to apply force to the first moving pivot in a second direction opposite to the first direction to pivot the second clamp jaw away from the first clamp jaw.

\* \* \* \* \*